US012691225B2

(12) United States Patent
Rivier et al.

(10) Patent No.: US 12,691,225 B2
(45) Date of Patent: Jul. 28, 2026

(54) VALVE STOPPER FOR A MEDICAL INJECTION DEVICE AND MEDICAL INJECTION DEVICE FOR INJECTING AT LEAST ONE COMPOSITION

(71) Applicant: Becton Dickinson France, Le Pont de Claix (FR)

(72) Inventors: Cédric Rivier, Voreppe (FR);
Guillaume Lehee, La Buisse (FR);
Nastasja Grillet, Cusy (FR);
Ferdinand Lavigne, Seyssinet-Pariset (FR); Jérémie Vaxelaire, Grenoble (FR)

(73) Assignee: Becton Dickinson France, Le Pont de Claix (FR)

( * ) Notice: Subject to any disclaimer, the term of this patent is extended or adjusted under 35 U.S.C. 154(b) by 794 days.

(21) Appl. No.: 17/434,103

(22) PCT Filed: Feb. 25, 2020

(86) PCT No.: PCT/EP2020/054902
§ 371 (c)(1),
(2) Date: Aug. 26, 2021

(87) PCT Pub. No.: WO2020/173938
PCT Pub. Date: Sep. 3, 2020

(65) Prior Publication Data
US 2022/0134003 A1 May 5, 2022

(30) Foreign Application Priority Data

Feb. 27, 2019 (EP) ..................................... 19305230
May 22, 2019 (EP) ..................................... 19305647

(51) Int. Cl.
*A61M 5/19* (2006.01)
*A61M 5/315* (2006.01)
(Continued)

(52) U.S. Cl.
CPC .......... *A61M 5/19* (2013.01); *A61M 5/31513* (2013.01); *A61M 39/24* (2013.01);
(Continued)

(58) Field of Classification Search
CPC .. A61M 2005/1787; A61M 2005/3128; A61M 2039/2426; A61M 5/19;
(Continued)

(56) References Cited

U.S. PATENT DOCUMENTS

| | | | |
|---|---|---|---|
| 4,252,118 A | 2/1981 | Richard et al. | |
| 4,543,093 A | 9/1985 | Christinger | |

(Continued)

FOREIGN PATENT DOCUMENTS

| | | |
|---|---|---|
| EP | 0815885 A1 | 1/1998 |
| EP | 1844804 A1 | 10/2007 |

(Continued)

*Primary Examiner* — Emily L Schmidt
*Assistant Examiner* — Samuel J Marrison
(74) *Attorney, Agent, or Firm* — The Webb Law Firm

(57) ABSTRACT

The invention relates to a valve stopper configured to be positioned inside a barrel of an injection device for injecting a composition through a distal, including: a membrane having a proximal and distal face, the membrane being configured to separate a, distal chamber of the barrel from a proximal chamber; a lateral wall extending from the membrane to define a distal cavity, the lateral wall having a circumferential sealing surface configured to sealingly engage the inner surface of the barrel; where the proximal face presents a concave shape and the membrane includes a notch extending through the membrane between the proximal and distal face, being configured to selectively create a fluid path through the membrane from the proximal face to the distal face depending on the pressure exerted by a composition onto the proximal face of the membrane for transferring fluid only from the second chamber to the first.

20 Claims, 12 Drawing Sheets

(51) Int. Cl.

| | | |
|---|---|---|
| *A61M 39/24* | (2006.01) | |
| *A61M 5/178* | (2006.01) | |
| *A61M 5/28* | (2006.01) | |
| *A61M 5/31* | (2006.01) | |

(52) U.S. Cl.
CPC ..... *A61M 2005/1787* (2013.01); *A61M 5/284* (2013.01); *A61M 2005/3128* (2013.01); *A61M 2039/2426* (2013.01)

(58) Field of Classification Search
CPC .......... A61M 39/24; A61M 2005/2462; A61M 2005/31598; A61M 2039/064; A61M 2039/0653; A61M 2039/066; A61M 5/2455; A61M 5/2459; A61M 5/31596
See application file for complete search history.

(56) References Cited

U.S. PATENT DOCUMENTS

| | | | |
|---|---|---|---|
| 4,929,230 | A | 5/1990 | Pfleger |
| 5,695,465 | A | 12/1997 | Zhu |
| 5,899,881 | A | 5/1999 | Grimard et al. |
| 6,997,910 | B2 | 2/2006 | Howlett et al. |
| 7,001,362 | B2 | 2/2006 | Vincent |
| 7,935,078 | B2 | 5/2011 | Horita et al. |
| 10,173,011 | B2 | 1/2019 | Lum et al. |
| 10,322,235 | B2 * | 6/2019 | Thorne, Jr. ....... A61M 5/31513 |
| 10,369,294 | B2 | 8/2019 | Abbott |
| 2004/0102738 | A1 * | 5/2004 | Dikeman ............... A61M 39/24 604/256 |
| 2005/0171490 | A1 * | 8/2005 | Weaver ................. A61M 39/24 604/247 |
| 2005/0245880 | A1 * | 11/2005 | Howlett ................ A61M 5/285 604/231 |
| 2006/0142701 | A1 | 6/2006 | Thorne, Jr. et al. |
| 2011/0087093 | A1 * | 4/2011 | Buiser ................... A61M 39/24 600/435 |
| 2011/0224611 | A1 | 9/2011 | Lum et al. |
| 2012/0265171 | A1 * | 10/2012 | Thorne, Jr. ............. A61M 5/19 604/207 |
| 2016/0346481 | A1 | 12/2016 | Haindl et al. |
| 2018/0093040 | A1 * | 4/2018 | Thorne, Jr. ............. A61M 5/19 |
| 2019/0022326 | A1 | 1/2019 | Tachikawa et al. |
| 2019/0358667 | A1 * | 11/2019 | Gaus ...................... B65D 47/10 |

FOREIGN PATENT DOCUMENTS

| | | | |
|---|---|---|---|
| EP | 2596245 | B1 | 4/2022 |
| JP | 2000210384 | A | 8/2000 |
| WO | 2002076534 | A1 | 10/2002 |
| WO | 2008045042 | A1 | 4/2008 |
| WO | 2013124669 | A1 | 8/2013 |
| WO | 2017170634 | A1 | 10/2017 |

* cited by examiner

VALVE STOPPER FOR A MEDICAL INJECTION DEVICE AND MEDICAL INJECTION DEVICE FOR INJECTING AT LEAST ONE COMPOSITION

CROSS-REFERENCE TO RELATED APPLICATIONS

This application is the United States national phase of International Application No. PCT/EP2020/054902 filed Feb. 25, 2020, and claims priority to European Patent Application Nos. 19305230.5 filed Feb. 27, 2019, and 19305647.0 filed May 22, 2019, the disclosures of which are hereby incorporated by reference in their entirety.

BACKGROUND OF THE DISCLOSURE

Field of the Disclosure

The disclosure relates to a valve stopper for a medical injection device, and a medical injection device comprising said valve stopper, for injecting at least one composition.

Description of Related Art

Prefilled injection devices are common containers to deliver drugs or vaccines to patients and include syringes, cartridges and autoinjectors or the like. They usually comprise a plunger stopper in gliding engagement into a container, the container being filled with a pharmaceutical composition in order to provide the practitioners with a ready-to-use injection device for patients.

A container has a substantially cylindrical shape, and comprises a proximal end able to be stoppered by a plunger stopper, a distal end wherein the pharmaceutical composition is expelled from the container, and a lateral wall extending between the proximal end and the distal end of the container. In practice, the plunger stopper is aimed at moving, upon the pressure exerted by a plunger, from a proximal end of the container towards the distal end of the container, thereby expelling the drug contained into the container.

When compared to empty injection devices that are filled with a vial-stored pharmaceutical composition just prior to the injection to the patient's body, the use of prefilled injection devices leads to several advantages. In particular, by limiting the preparation prior to the injection, the prefilled injection devices provide a reduction of medical dosing errors, a minimized risk of microbial contamination and an enhanced convenience of use for the practitioners. Furthermore, such prefilled containers may encourage and simplify self-administration by the patients which allows reducing the cost of therapy and increasing the patient adherence. Finally, prefilled injection devices reduce loss of valuable pharmaceutical composition that usually occurs when a pharmaceutical composition is transferred from a vial to a non-prefilled injection device. This results in a greater number of possible injections for a given manufacturing batch of pharmaceutical composition thus reducing buying and supply chain costs.

Prefilled injection devices can be used to carry out the injection of a plurality of compositions to a patient. In such case, the container comprises two chambers, including a first chamber adapted to contain a first composition and a second chamber adapted to contain a second composition. The two chambers are separated by a second stopper, usually referred to as a plug or a diaphragm, that prevents the compositions from passing from one chamber to the other and mixing.

The document WO 02/076534 discloses a device for dispensing two visco-elastic solutions having different properties. The device comprises a mobile diaphragm that separates two chambers, each containing a solution. The mobile diaphragm is provided with an opening of a small diameter that is sufficient to prevent the mixing of the two solutions before the first solution has been injected, while allowing subsequent injection of the second solution. Alternatively, the mobile diaphragm may be provided with a membrane adapted to be pierced by an inner spike provided inside the barrel, in the distal end of the barrel itself, so as to further ensure that the mixing of the two solutions before injection of the first solution is prevented.

This document thus discloses to pass the second solution through the mobile diaphragm, via an opening formed in the diaphragm itself. In order to ensure the sealing of the first chamber in view of the second solution, in other terms to prevent mixing of the two solutions before complete injection of the first composition, the opening has a small diameter. This renders the injection of the second solution difficult to carry out, due to the force that needs to be applied onto the plunger for passing said solution through the opening and expelling it.

Such drawback is especially important when the composition has a high viscosity, which is usually the case for visco-elastic solutions, and/or when the injection is carried out manually by a user that cannot push on the plunger strongly enough with his fingers, for example when suffering from rheumatoid arthritis or from any type of disease affecting the user's hand or fingers. The injection may be a self-injection or may be performed by a user, such as a healthcare professional, to another person. In the case of healthcare professionals performing repetitive injections of viscous pharmaceutical compositions to patients, the repetition of the same gesture requiring high force applied on the plunger to carry out the injection may cause repetitive strain injuries.

The document EP 1 844 804 discloses a multi-chamber syringe, comprising a barrel and a plug that separates two chambers, each containing a solution. The plug comprises two flanges adapted to contact the inner surface of the barrel. The proximal flange is provided with an eccentric protrusion that extends in the distal direction. At the end of the injection of the first solution, the eccentric protrusion abuts the distal end of the barrel, which induces a pivoting of the plug relative to the barrel. The second solution may thereby pass through a space formed between each of the two flanges of the plug and the inner surface of the barrel, and through a fluidic path formed on the lateral wall of the plug between the flanges.

This document thus discloses to pass the second solution along the lateral wall of the plug, and between the flanges of the plug and the inner surface of the barrel.

The previous drawback arising from the high force required to inject the second solution is not solved by the device of this document, since the user has to exert a force onto the plunger that is sufficient to make the plug pivot relative to the barrel. Moreover, the gaps between the flanges of the plug and the inner surface of the barrel are very small relative to the diameter of the barrel. Hence, the user has to exert a force onto the plunger that is sufficient to force the passage of the liquid through these gaps. Thus, the injection of the second solution requires an important effort from the user.

Moreover, the sealing of the two chambers provided by the plug may not be sufficient to prevent mixing of the two solutions during the injection of the first solution, since the flanges of the plug slide along the inner surface of the barrel. The friction of the flanges against the barrel may create an undesired gap between them through which the second solution may pass and mix with the first solution.

The document U.S. Pat. No. 6,997,910 discloses a multi-chamber syringe, comprising a barrel and a valve assembly that separates two chambers, each containing a solution. The valve assembly comprises two parts, including a valved stopper and a valve actuator. The valve actuator is inserted into a hollow volume provided in the valved stopper, for selectively opening or closing a slit forming a valve provided in the distal face of the valved stopper.

The structure of the valve assembly is very complex, which may be detrimental for the functioning of the valve assembly as well as its manufacturing. Such valve assembly also takes a lot of space inside the barrel, which may limit the gliding and increase the force that is necessary for carrying out the injection. Moreover, the valve actuator may not be deformable enough, which would strain the valved stopper (compression ratio) and would lead to a competition between ensuring the hermeticity of the valve assembly and allowing a low gliding force.

The document U.S. Pat. No. 4,929,230 discloses a hypo-dermic syringe comprising a piston that separates two cham-bers, each containing a solution. The piston comprises a wall provided with external ribs, and lugs extending from the distal face of the piston. When the pressure in the proximal chamber containing the second solution is high enough, the wall of the piston collapses and the second solution may pass through a space between the piston and the inner surface of the barrel of the syringe.

This document does not solve the problems above. More-over, the structure of the piston is complex and the volume of the piston is high which reduces the maximum volume of solution that can be injected. Similarly, the volume of the stopper may be high which also reduces the maximum volume of solution that can be injected.

Another problem that is not solved by any of the preced-ing documents concerns the dead volume. At the end of the injection of the second solution, in the more distal chamber, a small volume of the second solution remains in the chamber. This small volume is called the dead volume. The dead volume has to be taken into account when a very precise volume of solution has to be injected, which requires additional calculations, and may result in errors in the volume of solution that has been effectively injected.

SUMMARY OF THE DISCLOSURE

The disclosure aims to provide a valve stopper for a medical injection device, and an injection device comprising said valve stopper, for injecting at least one composition, preferably for sequentially injecting at least two composi-tions, which may be pharmaceutical compositions, that overcome the drawbacks of the known devices.

The disclosure especially aims to provide such a valve stopper and injection device, that allows the user to easily carry out injection of the second composition contained in the barrel of the injection device, as well as ensuring an optimal sealing for preventing the two compositions from mixing before the first composition has been entirely injected.

The disclosure also aims to provide such a valve stopper which presents a lower volume in comparison to the stoppers of the prior art, and which allows decreasing the dead volume of the injected composition.

To this end, one object of the disclosure is a valve stopper configured to be positioned inside a barrel of an injection device for injecting at least one composition through a distal end of the barrel, said valve stopper comprising:

a membrane comprising a proximal face and a distal face, the membrane being configured to separate a first, distal chamber of the barrel from a second, proximal chamber of the barrel, a lateral wall extending distally, or both distally and proximally, from the membrane to define at least a distal cavity, the lateral wall comprising a circumfer-ential sealing surface configured to sealingly engage the inner surface of the barrel, characterized in that the proximal face of the membrane presents a concave shape and the membrane comprises a notch extending through at least a part of the thickness of the membrane between the proximal face and the distal face, the notch being configured to selectively create a fluid path through the membrane from the proximal face to the distal face depending on the pressure exerted by a composition onto the proximal face of the membrane for transferring fluid only from the second chamber to the first chamber.

According to other optional features of the valve stopper:

the lateral wall comprises an inner recess configured to induce collapsing of the valve stopper under a mechani-cal pressure exerted in a distal direction;

the inner recess is an annular groove extending in the lateral wall along the circumference of the valve stop-per;

the valve stopper comprises three ribs, including a middle rib and two lateral ribs, and the membrane is aligned with the middle rib;

the notch extends only in a part of the thickness of the membrane, thereby delimiting a tear part in the thick-ness of the membrane that is not traversed by the notch, said tear part being configured to tear along the notch under a determined pressure exerted by the composi-tion to create the fluid path;

the tear part of the membrane forms a valve configured to open or close the cavity depending on the pressure exerted by the composition onto the proximal face of the membrane;

the notch extends through a part of the membrane from the distal face of the membrane;

the depth of the notch is superior or equal to 0.1 mm, preferably superior or equal to 0.2 mm;

the notch has an oblong shape, or is in the form of a cross comprising two segments that intersect at the center of the cross;

the notch is a split that extends through the membrane between the proximal face and the distal face, said split forming a valve configured to open or close the cavity depending on the pressure exerted by the composition onto the proximal face of the membrane;

the notch is in the form of a line passing through the center of the proximal face of the membrane;

the notch further comprises two segments, each segment extending on both sides of an end of the line;

the distal face of the membrane presents a planar or convex shape, the curvature of the distal face extending away from the proximal face;

the notch presents a length that is superior to a quarter of the diameter of the cavity and inferior to the diameter of said cavity.

Another object of the disclosure is a medical injection device for injecting at least one composition, comprising:

a barrel extending from a proximal end to a distal end, a plunger stopper adapted to be translationally movable inside the barrel, a valve stopper as described previously, arranged between the distal end of the barrel and the plunger stopper, adapted to be translationally movable inside the barrel, wherein the lateral wall of the valve stopper sealingly engages the inner surface of the barrel.

According to other optional features of the medical injection device:

the medical injection device is adapted to sequentially inject two compositions, wherein the valve stopper separates two chambers of the barrel including a first chamber between the valve stopper and the distal end of the barrel containing a first composition, and a second chamber between the valve stopper and the plunger stopper containing a second composition;

the valve stopper presents the successive following positions:

a rest position, wherein the fluid path is closed, a sealing position, wherein the valve stopper is more distal than in the rest position, wherein the fluid path is closed, the proximal face of the membrane being subjected to a pressure that is inferior to a valve opening force $F_{op}$ of the notch, an injection position, wherein the valve stopper abuts the distal end of the barrel, the fluid path being opened due to a pressure exerted on the proximal face of the membrane that is superior to the valve opening force $F_{op}$ of the notch;

the valve stopper further presents a collapsed position wherein the plunger stopper abuts the valve stopper and said valve stopper is collapsed;

the medical injection device is advantageously a syringe;

the proximal face of the membrane presents a radius of curvature which is from 1.2 to 2.3 times greater than an inner diameter of the barrel.

In this application, the "distal direction" is to be understood as meaning the direction of injection, with respect to the injection device. The distal direction corresponds to the travel direction of the valve stopper and the plunger stopper during the injection of the first composition and/or the second composition, said compositions contained initially in the barrel of the injection device being expelled from the injection device. The "proximal direction" is to be understood as meaning the opposite direction to said direction of injection.

BRIEF DESCRIPTION OF THE DRAWINGS

Further features and advantages of the disclosure will become apparent from the detailed description to follow, with reference to the appended drawings, in which.

DETAILED DESCRIPTION

The disclosure relates to a valve stopper 1 configured to be positioned inside a barrel 101 of an injection device 100 for injecting at least one composition, preferably for sequentially injecting at least two compositions. Such injection device 100 is particularly suited for performing the injection of pharmaceutical compositions, by a healthcare professional to a patient or by the patient himself in the case of a self-injection.

The composition is a fluid, and may be a liquid such as a pharmaceutical drug, a vaccine, etc. When the barrel is filled with said composition, gas may be present in said barrel (under the form of small bubbles) such as air, nitrogen, or another gas or mixture thereof.

Figure 1:
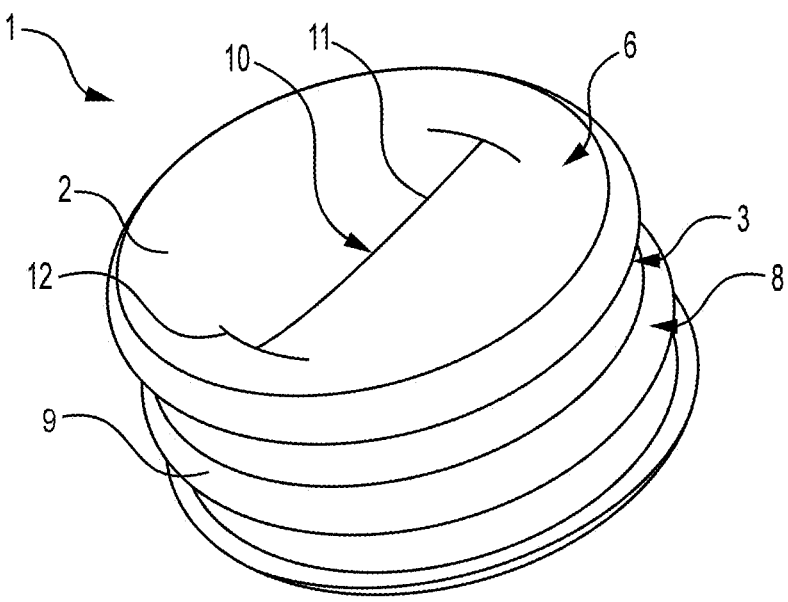
FIG. 1 is a perspective general view of the valve stopper according to the disclosure, according to a first general embodiment.
Figure 2:
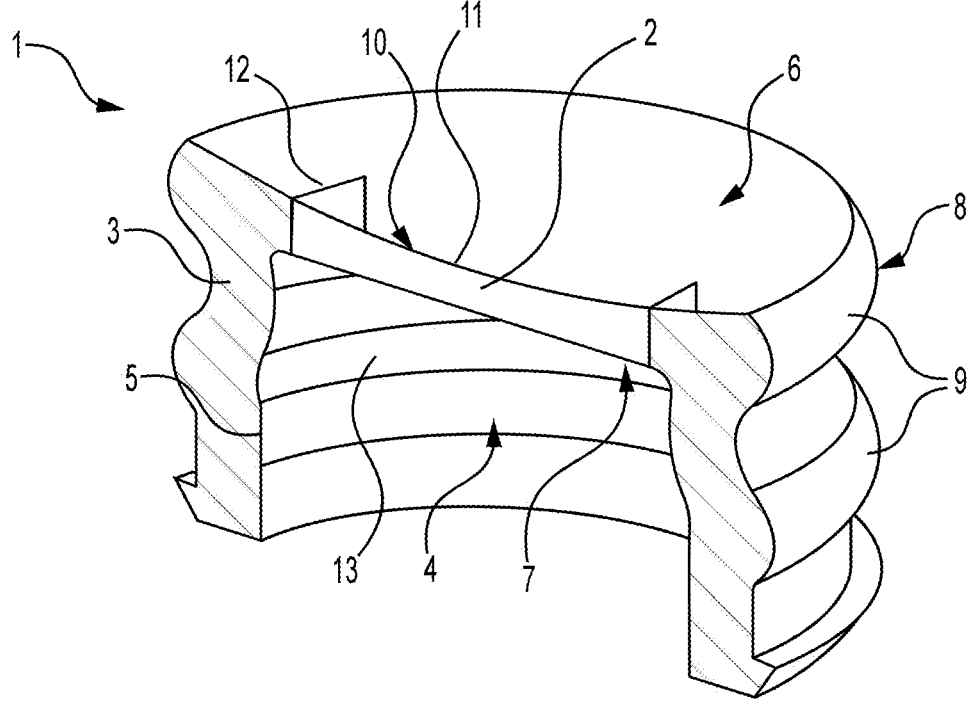
FIG. 2 is a sectional general view of the valve stopper of FIG. 1.

A first general embodiment of the valve stopper 1 according to the disclosure is illustrated in FIG. 1 as a general view and in FIG. 2 as a sectional view.

The valve stopper 1 has a substantially cylindrical shape, which corresponds to the shape of the barrel 101 of the injection device, such as a syringe, in which said valve stopper is intended to be inserted.

The valve stopper 1 comprises a membrane 2, which comprises a proximal face 6 and a distal face 7. A lateral wall 3 of the valve stopper extends distally, or both distally and proximally, from the membrane.

The lateral wall 3 defines a cavity 4, which is a hollow volume delimited by the inner face 5 of the lateral wall and the proximal face 6 or the distal face 7 of the membrane.

In the embodiment represented in FIGS. 1 and 2, the lateral wall 3 extends in the distal direction only, and the cavity 4 is delimited by the inner face 5 of the lateral wall and the proximal face 6 of the membrane that constitutes the bottom of the cavity.

According to another embodiment (not represented), the lateral wall 3 of the valve stopper extends both proximally and distally from the membrane 2. The membrane thereby separates two respective cavities, including a proximal cavity delimited by the inner face 5 of the lateral wall and the proximal face 6 of the membrane, and a distal cavity delimited by the inner face 5 of the lateral wall and the distal face 7 of the membrane.

The lateral wall 3 is advantageously provided with an outer sealing surface 8 configured to sealingly engage the inner wall of the barrel.

The sealing surface 8 is continuous, which means that it extends continuously along the circumference of the valve stopper and forms a ring. Since the continuous surface extends between the outer face of the lateral wall of the valve stopper 1 and the inner surface 102 of the barrel of the medical container, any passage of a composition between the valve stopper 1 and the barrel 101 is prevented. Optimal sealing is thus ensured.

According to a preferred embodiment, the sealing surface 8 may comprise two or more sealing ribs 9. The number of ribs as well as the dimensions of each rib, such as height, width, and the distance between two adjacent ribs, may be adapted to as to further optimize the sealing depending on the dimensions of the valve stopper and the barrel.

According to an embodiment (not represented), the valve stopper 1 comprises three ribs 9, including a middle rib and two lateral ribs, and the membrane is aligned with the middle rib. In this embodiment, the lateral wall 3 of the valve stopper extends both proximally and distally from the membrane and delimitates two cavities. The two lateral ribs are aligned with one of the two cavities respectively. According to another embodiment (not represented), the lateral wall 3 of the valve stopper mainly extends proximally from the membrane and a smaller part of the lateral wall protrudes and extends distally from the membrane. In this embodiment, the number of gas bubbles present in the composition comprised between the valve stopper 1 and the distal end of the barrel may be reduced.

The presence of two or more ribs reduces the contact surface between the lateral wall of the valve stopper and the inner surface of the barrel of the injection device, compared to a plane lateral wall of the valve stopper, thus improving the gliding performance of the valve stopper relative to the barrel. As a result, the force that needs to be exerted onto the valve stopper for displacing it inside the barrel is reduced which makes the injection easier for the user, and prevents the slip-stick effect that usually results from the sliding of the valve stopper relative to the barrel. Besides, the greater the distance between the ribs, the greater the stability of the valve stopper.

The proximal face 6 of the membrane presents a concave shape.

The distal face 7 of the membrane presents a planar or a convex shape.

Figure 3A:
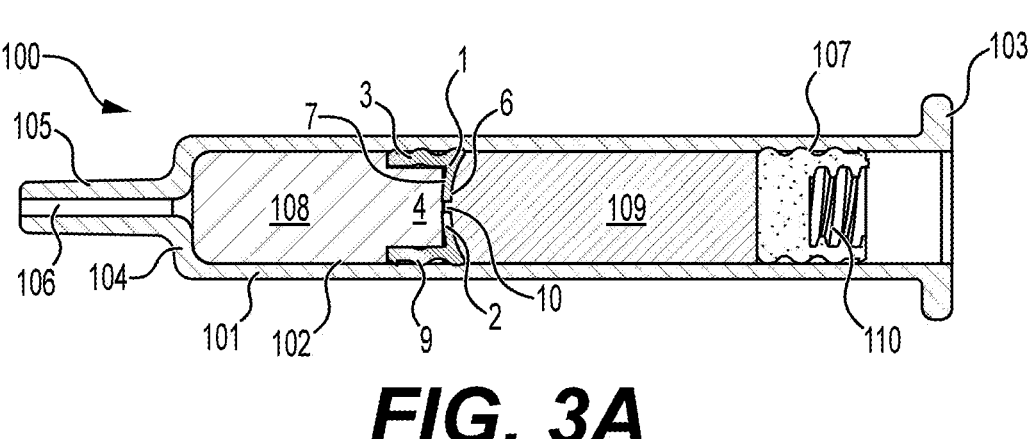
FIG. 3A is a sectional view of a medical injection device comprising a valve stopper that separates a first composition and a second composition, before injection of the first composition.
Figure 3B:
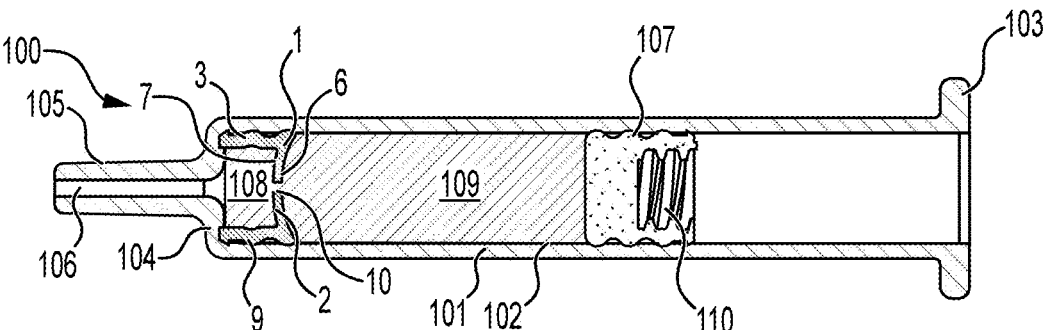
FIG. 3B is a sectional view of the medical injection device of FIG. 3A, at the end of the injection of the first composition.
Figure 3C:
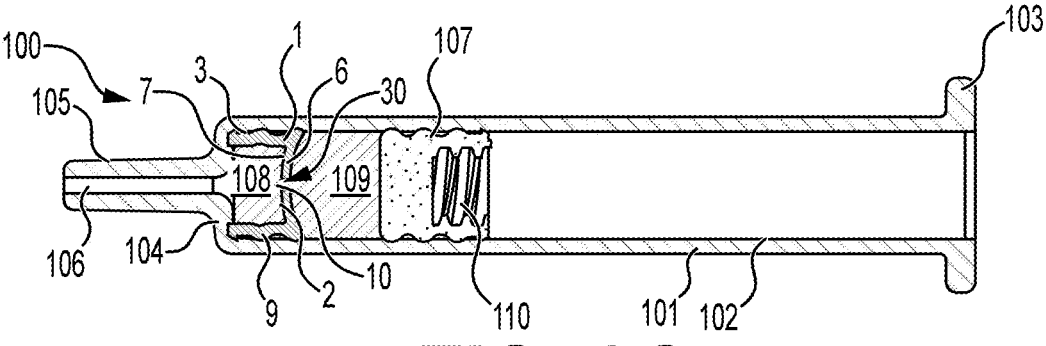
FIG. 3C is a sectional view of the medical injection device of FIG. 3A, during the injection of the second composition.
Figure 3D:
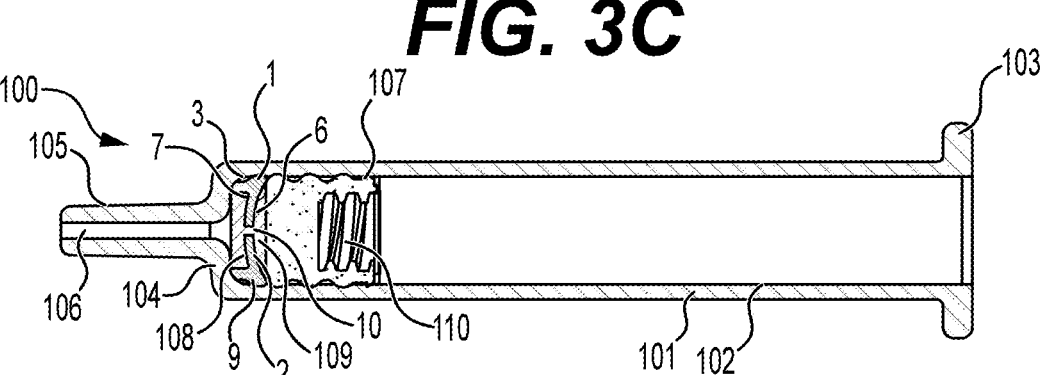
FIG. 3D is a sectional view of the medical injection device of FIG. 3A, at the end of the injection of the second composition, wherein the valve stopper is in the collapsed position.
Figure 3E:
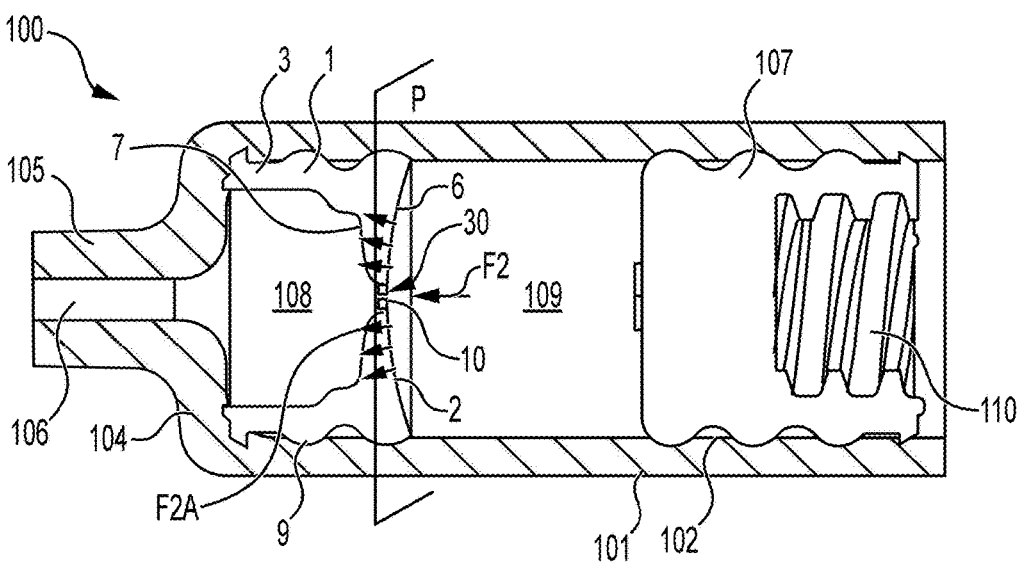
FIG. 3E is a cross sectional view of the valve stopper according to the first general embodiment, in a plane comprising the split, that illustrates the functioning of the check valve, the valve being open.
Figure 3F:
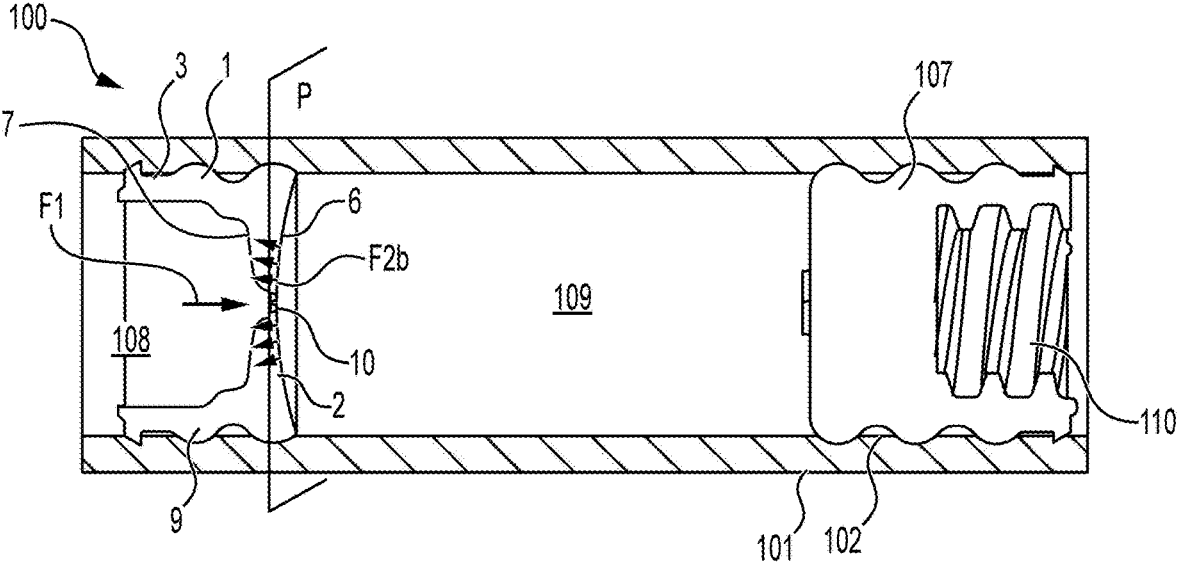
FIG. 3F is a view of the valve stopper according to the first general embodiment that illustrates the functioning of the check valve, the valve being closed.

The term "concave" related to a face of the membrane means that said face is curved and that the apex of the curvature is directed towards the plane P on FIG. 3E, which is a plane orthogonal to the distal-proximal direction and comprising the middle of the thickness of the membrane in the thinnest region thereof. Conversely, the term "convex" related to a face of the membrane means that said face is curved and that the apex of the curvature extends away from the plane P.

Hence, the apex of the curvature of the proximal face of the membrane, presenting a concave shape, extends towards the distal face of the membrane. In the case the distal face of the membrane presents a convex shape, the apex of the curvature of said distal face extends away from the proximal face of the membrane.

The membrane 2 comprises a notch. Said notch extends through at least a part of the thickness of the membrane between the proximal face 6 and the distal face 7 of the membrane 2. The notch is configured to create a fluid path 30 through the membrane 2 from the proximal 6 to the distal face 7 of the membrane 2. According to the first general embodiment, the notch is a split 10 that extends through the membrane between the proximal face 6 and the distal face 7. The split 10 forms a valve configured to open or close the cavity 4 depending on the pressure exerted by a composition onto the proximal face 6 of the membrane.

The valve stopper may be made of any material with elastomeric properties usually used to manufacture stoppers for medical injection devices. For example, the valve stopper may be made of elastomer, rubber, thermoplastic elastomer, and liquid silicon rubber.

The split 10 is preferably in the form of a line 11 passing through the center of the proximal face of the membrane, preferably a straight line. Such line is quite simple to manufacture. The membrane may be manufactured without any split, and then pierced to form the split. Alternatively, the split may be formed in the membrane directly during the manufacture of the membrane.

The length of the split 11 is preferably is superior to a quarter of the diameter of the cavity, and inferior to the diameter of the cavity 4. A length inferior to a quarter of the diameter of the cavity would require a very high force from the user for opening the valve, thereby making the injection harder to carry out. On the contrary, a length superior to the diameter of the cavity would render the parts of the split that do not lead to the cavity useless and may deteriorate the functioning of the split.

According to an embodiment, the split 10 further comprises two segments 12, each segment extending on both sides of an end of the line 11, thereby forming a capital "i". This embodiment achieves a greater opening of the split. In FIG. 1, the two segments 12 are substantially perpendicular to the line 11 of the split, and preferably slightly curved to match the curvature of the membrane, which facilitates the opening of the split 10.

Advantageously, the membrane 2 of the valve stopper has a thickness that is comprised between 0.3 mm and 1 mm. Preferably the valve stopper is used in an injection device having an injection volume comprised between 1 mL and 3 mL, wherein the thickness of the membrane 2 is comprised between 0.4 mm and 0.8 mm, preferably the thickness of the membrane 2 is superior or equal to 0.5 mm, preferably superior or equal to 0.6 mm.

The membrane 2 is a one-way membrane, which means that the membrane is configured to allow a composition to pass through the membrane via the open split 10 only when said composition flows in the distal direction, meaning the direction of injection. In other terms, the split is configured to open only for allowing the composition to pass through the membrane from one side of the valve stopper where the composition contacts the proximal face 6 of the membrane, to another side of the valve stopper where the composition contacts the distal face 7 of the membrane. The split 10 is configured to remain closed for preventing a composition to pass through the membrane from the other side of the valve stopper where the composition contacts the distal face 7 of the membrane to the one side of the valve stopper where the composition contacts the proximal face 6 of the membrane, namely in the proximal direction which is the direction opposite to the direction of injection. Such valve is called "check valve".

The split 10 presents a valve opening force $F_{op}$, which corresponds to the force that needs to be exerted onto the proximal face of the membrane for opening the split. The valve opening force thus corresponds to an opening threshold of the split. The valve opening force is preferably comprised between 10 N and 25 N, preferably between 10N and 20N, more preferably between 15 N and 20 N. The split 10 is configured to remain closed as long as the pressure P2 exerted onto the proximal face 6 of the membrane is inferior to $F_{op}$, and to open when said pressure P2 is equal or superior to $F_{op}$ thereby allowing the injection of the composition located initially proximally relative to the valve stopper.

The concave shape of the proximal face of the membrane minimizes the valve opening force $F_{op}$, thereby facilitating the opening of the valve and the subsequent injection of a composition located proximally relative to the valve stopper, while allowing the valve to function as a check valve.

According to calculations made by the inventors, the radius of curvature of the concave face of the membrane is preferably about 1.8 time±30% greater (i.e. between 1.2 time and 2.3 times greater) than the inside diameter of the barrel of the syringe. This ratio between the radius of curvature of the proximal face and the inside diameter of the barrel is optimized in order to limit the force required to open the valve for the injection.

The shape of the split has an impact on the injection force of the second liquid. The smaller the split, the higher the injection force.

The lateral wall 3 of the valve stopper advantageously comprises an inner recess 13 configured to induce collapsing of the valve stopper 1 under a mechanical pressure exerted in a distal direction.

In the embodiment of FIG. 2, the at least one recess 13 is an annular groove that extends in the lateral wall 3 along the circumference of the valve stopper. Preferably only recess 13 extends in the lateral wall 3. The annular groove is preferably aligned with a rib 9, and more preferably aligned with the middle rib when the number of ribs is odd.

The presence of the inner recess 13 allows the collapsing of the stopper and thus reduces the dead volume, which correspond to the volume of a composition that remains inside the barrel 101 in contact with and distally relative to the valve stopper after its injection. This enables increasing the total volume of the injected composition, and prevents waste of composition.

A second general embodiment of the valve stopper 1 according to the disclosure is illustrated in FIGS. 4-11 and 14-15, wherein FIGS. 4-7 and 14 are directed to a first embodiment of the valve stopper and FIGS. 8-11 and 15 are directed to a second embodiment of the valve stopper.

The general structure of the valve stopper of the second general embodiment is similar to that of the first general embodiment described before, and will not be further described. The common features between the first and the second general embodiments represented in FIGS. 1-3 and 4-11 are given the same references.

An advantage of the second general embodiment over the first general embodiment is that the membrane keeps its structural integrity during the fabrication process of the valve stopper, which renders said process easier to carry out, especially when steps involving vacuum are performed.

According to the second general embodiment, the notch 20 extends only in a part of the thickness of the membrane 2. The part 21 of the thickness of the membrane, which is not traversed by the notch, called tear part, is configured to tear along the notch under a determined pressure exerted by the composition so as to create a fluid path 30 through the membrane 2 from the proximal face 6 to the distal face 7.

To do so, the notch 20 forms a localized weakened zone in the membrane 2, which causes the membrane to tear when a determined pressure is applied onto said one of its proximal face by the composition to be injected. When torn, the tear part 21 also acts as a guide for the flow of the composition along the fluidic path thus formed.

The tear part 21 forms a valve configured to open or close the cavity 4 depending on the pressure exerted by the composition onto the proximal face 6 of the membrane 2.

The notch 20 extends through a part of the membrane 2 preferably from the distal face 7 of the membrane. The notch may alternatively extend from the proximal face 6 of the membrane.

Preferably the valve stopper is used in an injection device having an injection volume comprised between 1 mL and 3 mL, wherein the thickness of the membrane 2 is comprised between 0.4 mm and 0.8 mm, preferably the thickness of the membrane 2 is superior or equal to 0.5 mm, and more preferably superior or equal to 0.6 mm.

The depth of the notch 20 is preferably comprised between about 25% and 50% of the thickness of the membrane, more preferably between 25% and 35% of the thickness of the membrane. For a membrane having a thickness of about 0.5 mm, the depth of the notch 20 is preferably superior or equal to 0.1 mm, more preferably superior or equal to 0.2 mm. This facilitates the tearing of the membrane, by lowering the pressure exerted by the composition that is needed to tear said membrane.

Similarly to the first general embodiment, the membrane 2 according to the second general embodiment is a one-way membrane configured to allow a composition to pass through the membrane via the notch 20 only when said composition flows in the distal direction, meaning the direction of injection. In other terms, the tear part 21 is configured to open only for allowing the composition to pass through the membrane from one side of the valve stopper where the composition contacts the proximal face 6 of the membrane, to another side of the valve stopper where the composition contacts the distal face 7 of the membrane. The tear part 21 of the membrane is thereby configured to act as a check valve.

The tear part 21 is configured to remain closed as long as the pressure P2 exerted onto the proximal face 6 of the membrane is inferior to the valve opening force $F_{op}$, and to open by tearing when said pressure P2 is equal or superior to $F_{op}$ thereby creating a fluid path through the membrane and allowing the injection of the composition located initially proximally relative to the valve stopper.

According to a first embodiment of the second general embodiment, illustrated in FIGS. 4-7, the notch has an oblong form. The oblong form comprises two opposite sloped surfaces 22 that join at a common line 23. The two opposite sloped surfaces 22 are laterally joined by two conical ends 24. The common line contacts the tear part 21 of the membrane, and constitutes the starting point of the tearing.

As such, when the pressure exerted by the composition onto the membrane is superior to the valve opening force $F_{op}$, the common line 23 tears and induces the tearing of the tear part 21 of the membrane 2. This creates the fluidic path through the membrane.

The direction of inclination of the two sloped surfaces 22 depends on the face of the membrane the notch extends therefrom. When the notch 20 extends from the distal face 7 of the membrane, the sloped surfaces 22 are directed toward the proximal direction, opposite the direction of injection of the composition. Conversely, when the notch 20 extends from the proximal face 6 of the membrane, the sloped surfaces 22 are directed toward the distal direction, in the direction of injection of the composition.

Figure 4:
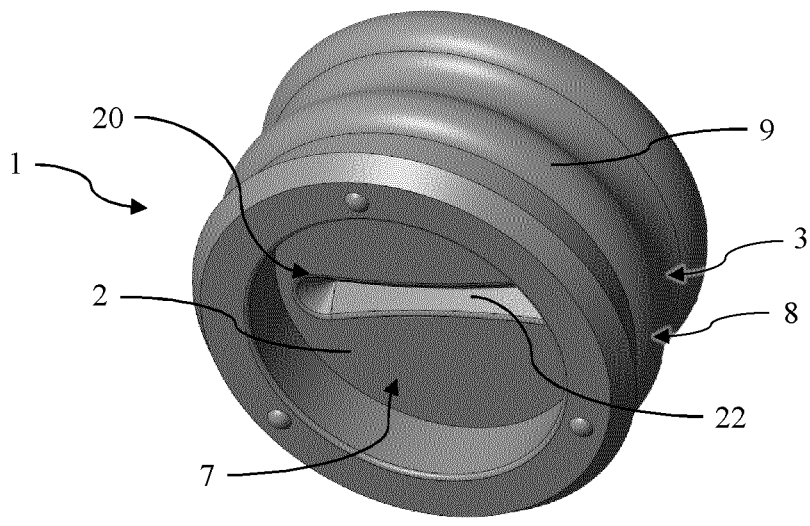
FIG. 4 is a perspective general view of the valve stopper of the disclosure, according to a first embodiment of a second general embodiment.
Figure 5:
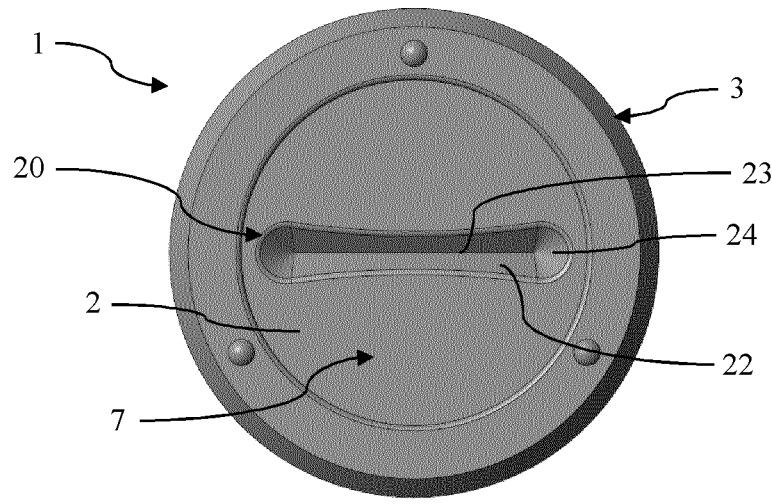
FIG. 5 is a view of the distal face of the valve stopper of FIG. 4.
Figure 6:
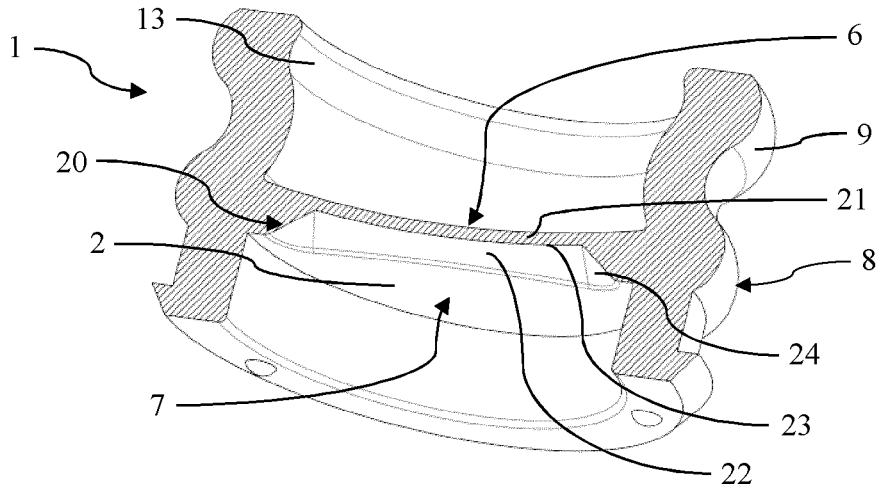
FIG. 6 is a sectional general view of the valve stopper of FIG. 4.
Figure 7:
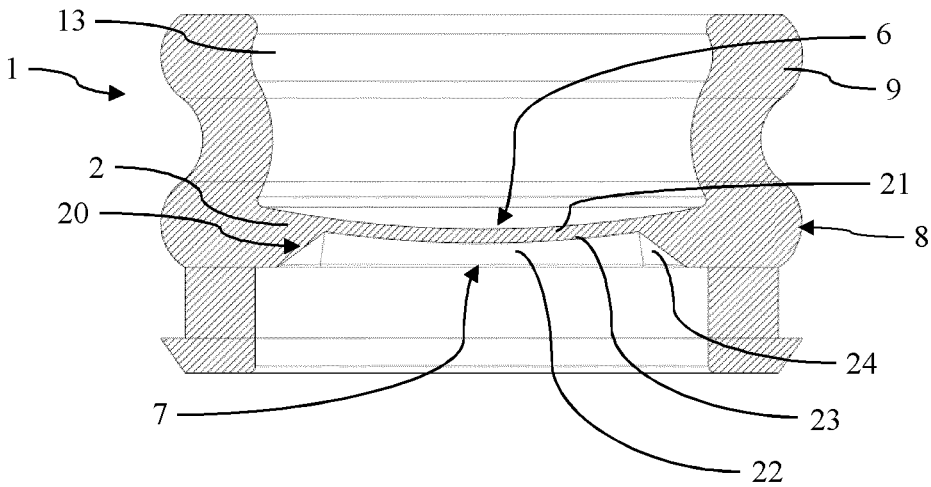
FIG. 7 is a side sectional general view of the valve stopper of FIG. 4.
Figure 8:
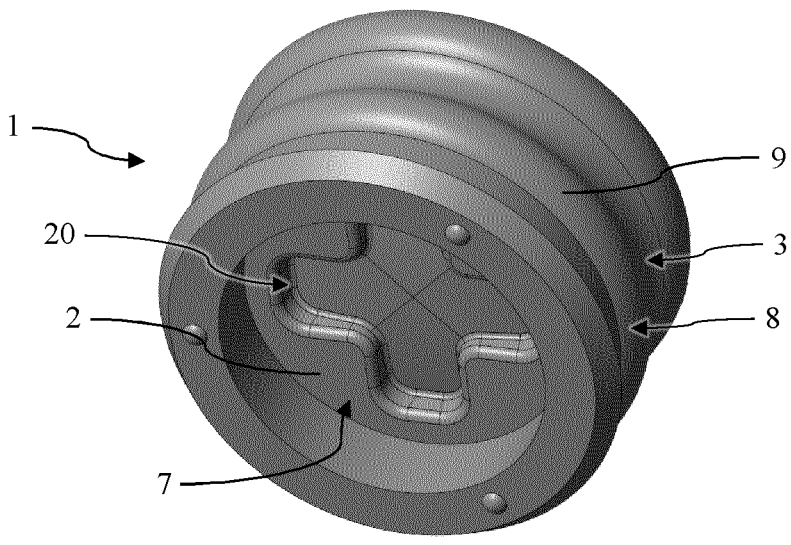
FIG. 8 is a perspective general view of the valve stopper of the disclosure, according to a second embodiment of the second general embodiment.
Figure 9:
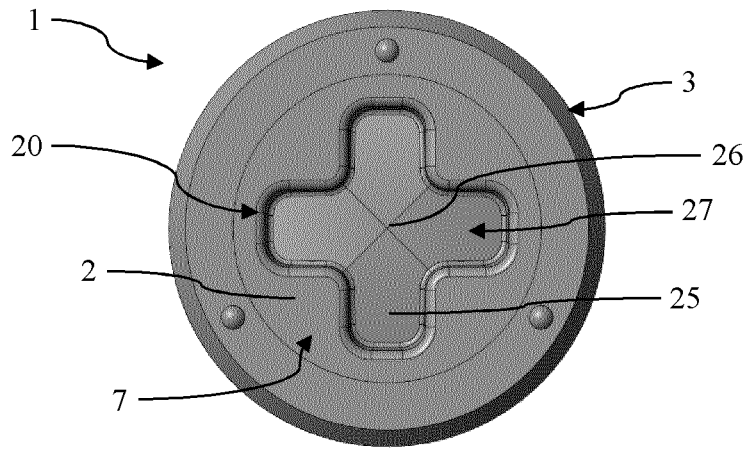
FIG. 9 is a view of the distal face of the valve stopper of FIG. 8.
Figure 10:
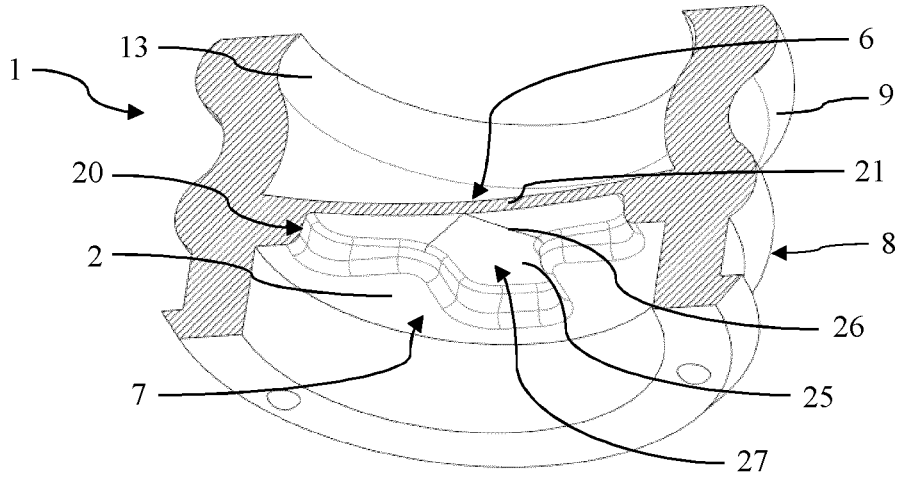
FIG. 10 is a sectional general view of the valve stopper of FIG. 8.
Figure 11:
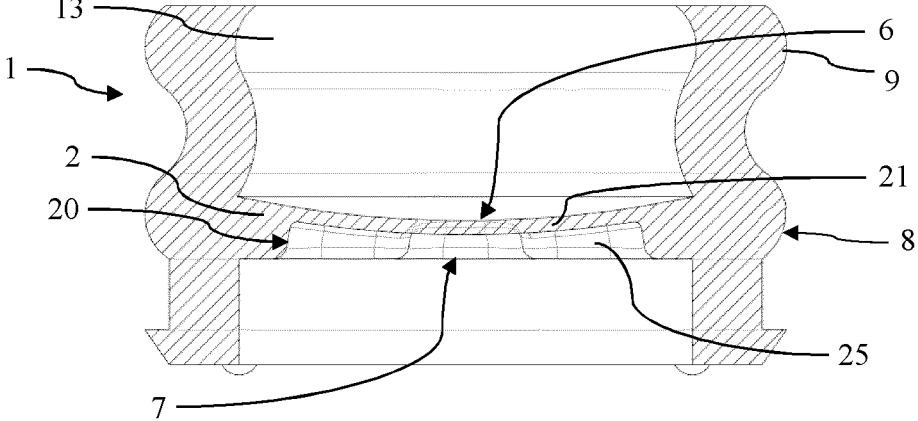
FIG. 11 is a side sectional general view of the valve stopper of FIG. 8.

Different structural variations may be made to the oblong notch. For example, the two conical ends 24 may be replaced by two straight walls parallel to each other. Moreover, the intersection of the sloped surfaces with the proximal or distal surface of the membrane, which from the longitudinal sides of the oblong shape, may slightly bend toward each other as illustrated in FIGS. 4 and 5, or may be straight and parallel to each other.

According to a second embodiment of the second general embodiment, illustrated in FIGS. 8-11, the notch 20 is in the form of a cross. The cross comprises two perpendicular segments 25 that intersect at the center of the cross. The membrane preferably tears only at the center of the cross. The center is represented by another cross in fine lines in FIGS. 8 and 9, called central cross 26, which is optional. The central cross 26 contacts the tear part 21 of the membrane, and may constitute the starting point of the tearing. Of course, the cross 20 may tear entirely in one go, with the central cross 26 (when present) and the two perpendicular segments 25 tearing substantially at the same time.

As such, when the pressure exerted by the composition onto the membrane is superior to the valve opening force $F_{op}$, the cross 20 tears and induces the tearing of the tear part 21 of the membrane. This creates the fluidic path through the membrane. Preferably, only the central cross 26 tears, and the protruding portions 27 of the cross that delimit the central cross do not tear but may deform so as to follow the tearing of the central cross and to guide the flow of the composition along the fluidic path thus formed.

The dimensions of the notch 20, such as its length, width, and depth, may be adapted to adjust the injection force required for injecting the second composition. Concerning the first embodiment of the second general embodiment, the length and the width of the oblong shape, the inclination angle of the sloped surfaces may be adapted accordingly. Concerning the second embodiment of the second general embodiment, the length and the width of the two segments of the cross may be adjusted accordingly as well.

The valve stopper 1 of the disclosure is configured to be positioned inside the barrel 101 of an injection device 100 for injecting at least one composition, and preferably sequentially injecting at least two compositions. An embodiment of such injection device is illustrated in FIG. 3A.

In reference to FIG. 3A, the injection device 100 is a syringe comprising a barrel 101 that extends from a proximal end 103 to a distal end 104. The distal end is provided with a tip 105 which encloses a channel 106 for the passage of a composition.

The injection device 100 comprises a plunger stopper 107 adapted to be translationally movable inside the barrel for injecting a composition. The plunger stopper advantageously comprises a hollow volume 110 having a shape that corresponds to that of the head of a plunger rod in order to accommodate said head when said plunger rod pushes the plunger stopper in the distal direction to perform an injection.

The valve stopper 1 is arranged between the distal end 104 of the barrel and the plunger stopper 107, and is translationally movable inside the barrel 101. The valve stopper 1 separates two chambers of the barrel, including a first chamber 108 between the valve stopper 1 and the distal end 104 of the barrel, and a second chamber 109 between valve stopper 1 and the plunger stopper 107.

The first chamber 108 contains a first composition, which is intended to be injected first, and the second chamber 109 contains a second composition, which is intended to be injected after the first composition has been injected.

The first and the second compositions may be the same or different. Such compositions may be pharmaceutical, and may be visco-elastic.

Note that the injection device 100 may comprise more than one valve stopper 1, and may be used to inject more than two compositions. For example, the injection device may comprise two valve stoppers, including a first valve stopper separating a first chamber located between the distal end of the barrel and said first valve stopper and a second chamber located between said first valve stopper and a second valve stopper, said second valve stopper separating the second chamber and a third chamber located between the second valve stopper and the plunger stopper. Each of the first, second, and third chambers contains a composition.

Before injection, the split 10 is closed, which means that when the valve stopper 1 is inserted in the barrel 101 of the injection device, the split 10 is maintained closed under radial compression of the valve stopper, said valve stopper being itself subjected to radial compression of the barrel. The closed split 10 prevents the mixing of the first and second compositions, by preventing the first composition from entering the second chamber 109 and the second composition from entering the first chamber 108.

The two or more ribs 9 of the valve stopper sealingly engages the inner surface 102 of the barrel. Hence, the first and the second composition cannot pass from a chamber to another via a passage between the valve stopper 1 and the barrel 101.

The functioning of the valve stopper and the injection device comprising said valve stopper will now be described in the following of the present text, in reference to FIGS. 3A to 3D.

The following steps will be described in parallel for both the first general embodiment and the second general embodiment of the notch.

FIG. 3A correspond to the configuration of the injection device 100 before injection of the first composition.

In this configuration, the valve stopper 1 is in a rest position wherein the fluid path is closed. Concerning the first general embodiment, in the rest position, the split 10 is maintained closed under radial compression of the valve stopper, and the plunger stopper 107 is in a proximal position. Concerning the second general embodiment, in the rest position, the tear part 21 of the membrane is structurally intact, and thus the cavity 4 is closed.

The pressure P1 in the first chamber 108 and the pressure P2 in the second chamber 109 are substantially equal, such that the differential pressure ΔP=P2−P1 is substantially null, and thus much lower than the valve opening force $F_{op}$ of the split. The notch thus remains closed.

The user performs the injection of the first composition. The configuration of the injection device 100 is between that of FIGS. 3A and 3B. The force applied to the plunger stopper 107 is transmitted to the second chamber 109 and then to the valve stopper 1, which results in a force F2 exerted by the second composition onto the proximal face of the membrane 2 of the valve stopper.

The displacement of the valve stopper 1 in the distal direction pushes the first composition in the distal direction and said first composition is expelled from the syringe by the channel 106 of the tip. In this configuration, the valve stopper 1 is in a sealing position.

The displacement of the valve stopper 1 builds up pressure in the first chamber 108, since the diameter of the channel 106 is much smaller than the diameter of the barrel 101. This increase of the pressure P1 not only forces the first composition through the channel for injection, but also applies onto the distal face 7 of the membrane of the valve stopper in opposition to the displacement of the valve stopper. As a result, the valve stopper 1 is subjected to substantially equal and opposite pressures P1 and P2 respectively exerted by the first composition and the second composition onto the proximal face 6 and the distal face 7 of the membrane of the valve stopper.

As a consequence, the differential pressure ΔP is substantially null, and thus much lower than the valve opening force $F_{op}$ of the notch. During the displacement of the valve stopper 1, the differential pressure ΔP may not be substantially null but remains lower than the valve opening force $F_{op}$ of the notch. The split 10 of the first general embodiment thus remains closed. The tear part 21 of the second general embodiment remains intact.

The injection continues until the valve stopper 1 abuts the distal end 104 of the barrel, as illustrated in FIG. 3B. A fraction of the first composition still remains in the first chamber 108.

Since the valve stopper 1 cannot move further distally, the pressure P2 in the second chamber 109 increases and the force differential ΔP becomes superior to the valve opening force $F_{op}$.

As a result, concerning the first general embodiment, the split opens, thereby allowing the second composition to pass through said split up to the channel for the injection, as illustrated in FIG. 3C. In this configuration, the valve stopper is in an injection position.

This situation is also represented in more details in FIG. 3E, wherein the force exerted by the second composition onto the membrane 2 is represented by the arrow F2, and the force for opening the valve is illustrated by the smaller arrows F2a.

Concerning the second general embodiment, the tear part 21 tears, thereby creating a fluid path 30 through the membrane that allows the second composition to pass along the fluid path, through the notch and the tear part 21 which is torn, to the channel for the injection.

Figure 12A:
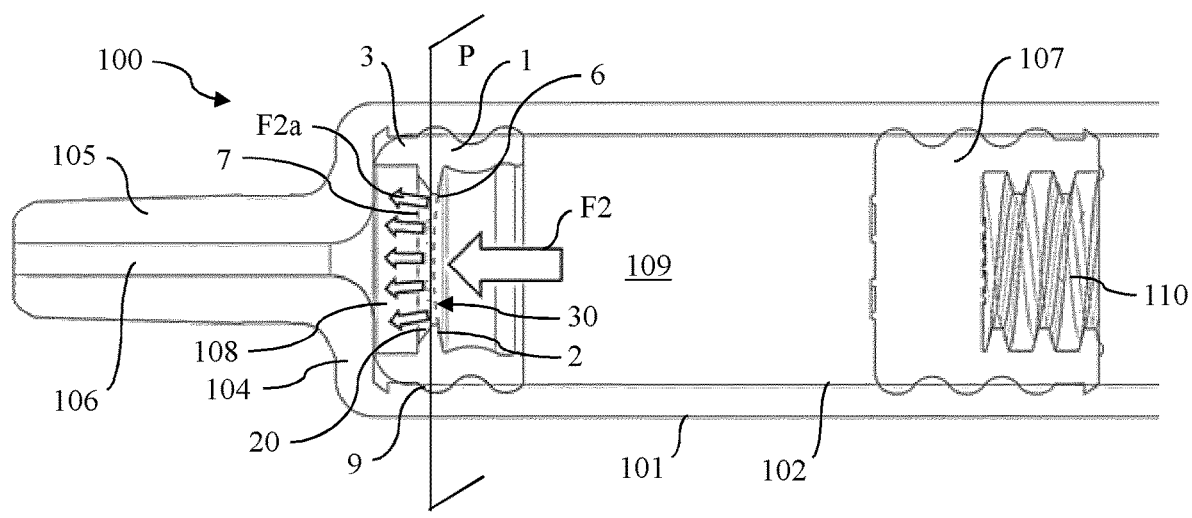
FIG. 12A is a cross sectional view of the valve stopper according to the first embodiment of the second general embodiment in a plane comprising the notch, that illustrates the creation of a fluid path through the membrane of the valve stopper.
Figure 13A:
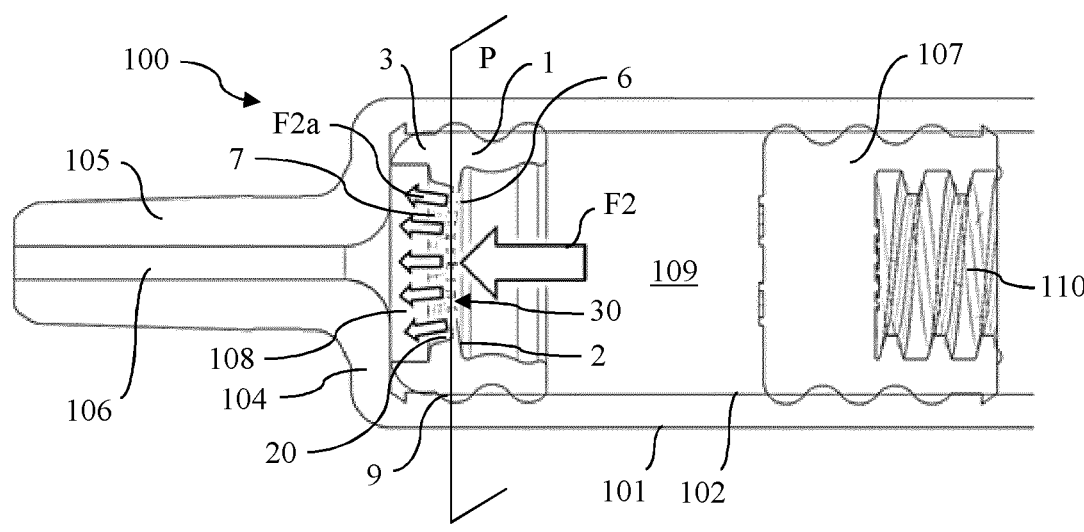
FIG. 13A is a cross sectional view of the valve stopper according to the second embodiment of the second general embodiment, in a plane comprising the notch, that illustrates the creation of a fluid path through the membrane of the valve stopper.

This situation is also represented in more details in FIGS. 12A and 13A for the first and the second embodiments of the second general embodiment, wherein the force exerted by the second composition onto the membrane 2 is represented by the arrow F2, and the force for opening the fluid path is illustrated by the smaller arrows F2a. The fluid path 30 is illustrated by the dotted line.

Figure 14:
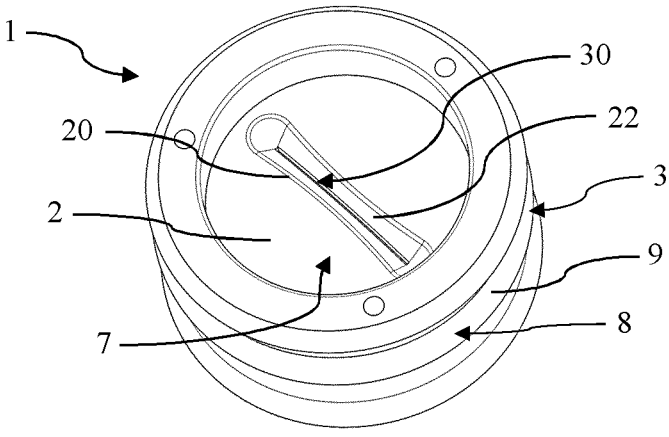
FIG. 14 is a perspective general view of the valve stopper according to the first embodiment of the second general embodiment, wherein a fluid path opens through the membrane.
Figure 15:
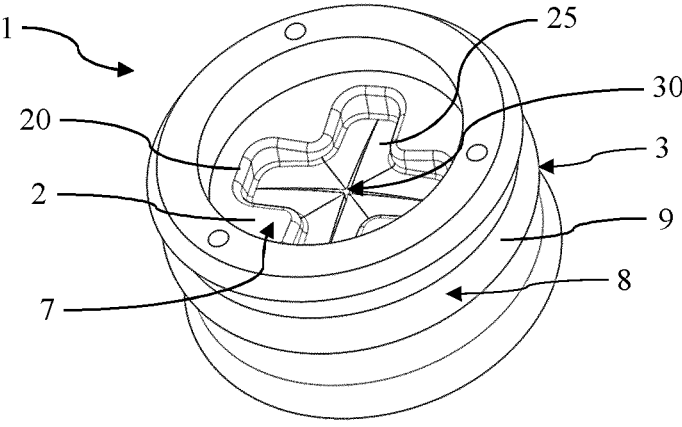
FIG. 15 is a perspective general view of the valve stopper according to the second embodiment of the second general embodiment, wherein a fluid path opens through the membrane.

FIGS. 14 and 15 show the opening of the fluid path 30 for the first and the second embodiments of the second general embodiment, with general perspective views of the valve stopper.

In this configuration, the valve stopper is in the injection position.

As previously explained, at this moment, a fraction of the first composition remains in the first chamber 108. Accordingly, at the beginning of the injection of the second composition, a fraction of the first composition and a small amount of the second composition may be mixed up since both compositions are injected through the same fluid path.

At the end of the injection of the second composition, the plunger stopper 107 abuts the valve stopper 1. A fraction of the second composition remains in the first chamber 108, that corresponds to the dead volume.

The valve stopper 1 collapses under the pressure exerted by the plunger stopper 107, the collapsing being set off thanks to the inner recess. The valve stopper is thus in a collapsed position, as illustrated in FIG. 3D. The collapsing of the valve stopper reduces the volume of the cavity 4, and the dead volume is thus injected.

In the case (not illustrated) where the valve stopper comprises a proximal cavity, the plunger stopper may advantageously comprise a distal pin fitting said proximal cavity. In this way, the engagement of said pin into the proximal cavity of the valve stopper allows expelling the second composition from the proximal cavity through the split.

According to an embodiment, the valve stopper in rest position contacts the distal end of the syringe. In this configuration, the volume of the first chamber is minimized. The second chamber contains a composition to be injected. This configuration is particularly useful when only one composition, especially a drug, is to be injected, and said drug (for example epinephrine) is very sensitive to contaminants and thus needs an additional protection from glue/metal (of the needle for example) or air.

According to a preferred embodiment, the valve stopper is moved in the proximal direction in order to generate a suction effect and to allow for filling the first chamber, which is empty, with a composition. This composition is typically blood or another drug, and in this case, this operation is called a "vein test" or a "reconstitution".

Figure 12B:
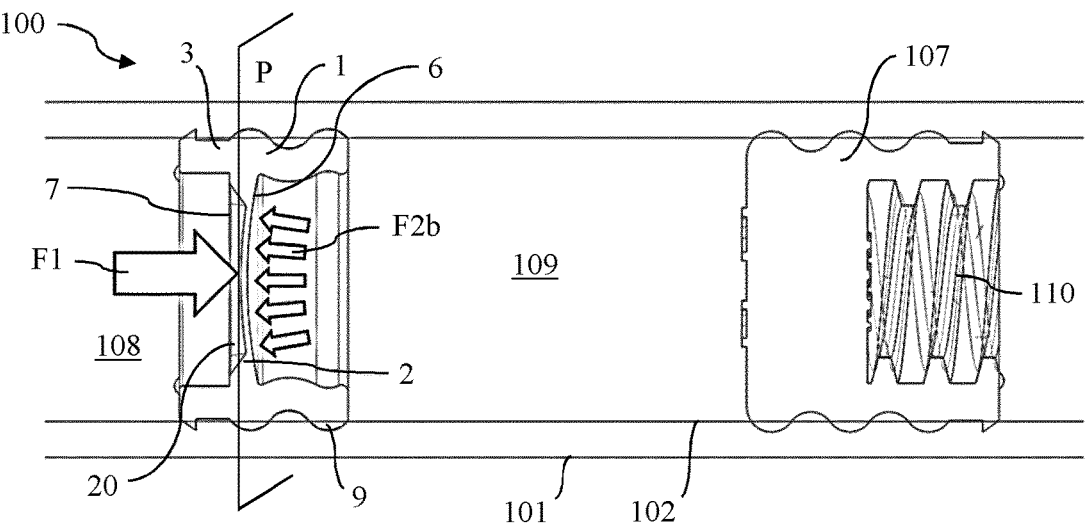
FIG. 12B is a cross sectional view of the valve stopper according to the first embodiment of the second general embodiment, wherein the fluid path is closed.
Figure 13B:
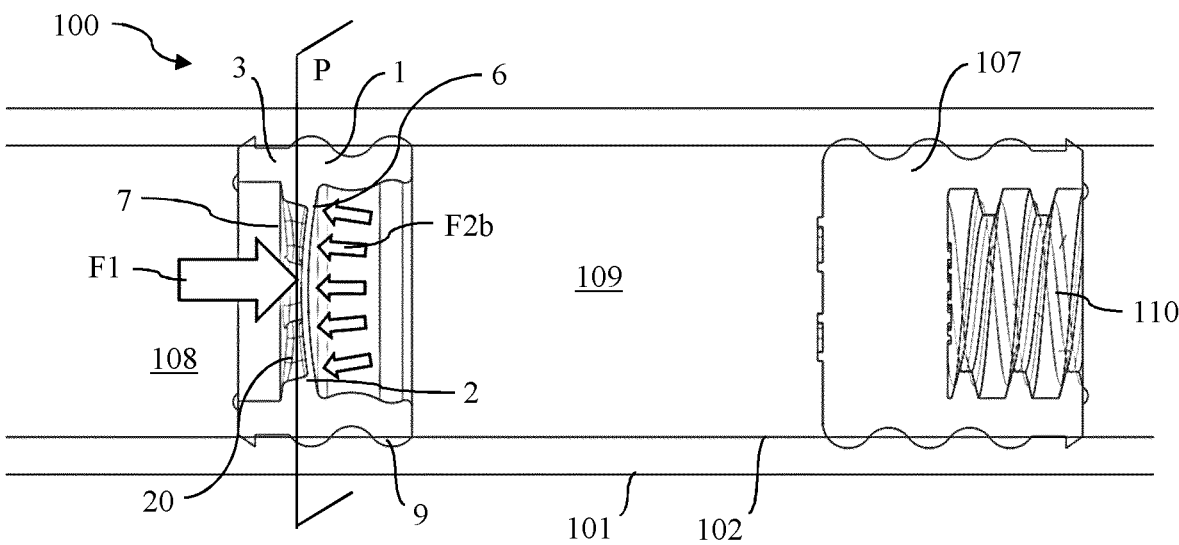
FIG. 13B is a cross sectional view of the valve stopper according to the second embodiment of the second general embodiment, wherein the fluid path is closed.

During the vein test or reconstitution, the notch remains closed thanks to the check valve function (FIGS. 3F, 12B, and 13B), thereby preventing mixing of the composition sucked with the first composition. The aspiration force is represented by the arrow F1, and the force exerted by the second composition onto the membrane, which maintains the fluid path closed, is represented by the smaller arrows F2*b*.

The vein test or reconstitution may be carried out before the injection of the first composition. In this case, another valve stopper is provided between the distal end of the barrel and the first composition.

Alternatively, the vein test or reconstitution may be carried out during the injection of the first composition. In this case, the injection is momentarily stopped, and the vein test is performed. The injection of the first composition then resumes.

The disclosure also relates to a medical injection device 100 for injecting at least one composition. Said medical injection device comprises a barrel 101 extending from a proximal end 103 to a distal end 104, a plunger stopper 107 adapted to be translationally movable inside the barrel 101, a valve stopper 1 as previously described, arranged between the distal end 104 of the barrel and the plunger stopper 107, and adapted to be translationally movable inside the barrel 101, wherein the lateral wall 3 of the valve stopper 1 sealingly engages the inner surface 102 of the barrel.

EXAMPLES

Measurement of the Injection Force

Tests have been performed to determine the injection force of the valve stopper according to the disclosure according to the first general embodiment, and of a stopper known in the state of the art.

The stopper known in the state of the art for example in U.S. Pat. No. 4,929,230, comprises ribs that extends radially outwardly along the circumference of the stopper. When said stopper is used, the composition is intended to pass through a passage between the ribs and the inner surface of the barrel. The legacy design does not comprise any split. The total volume of said stopper known in the state of the art is about 421 mm$^3$. As a comparison, the total volume of the valve stopper of the disclosure is about 162 mm$^3$.

Figure 16:
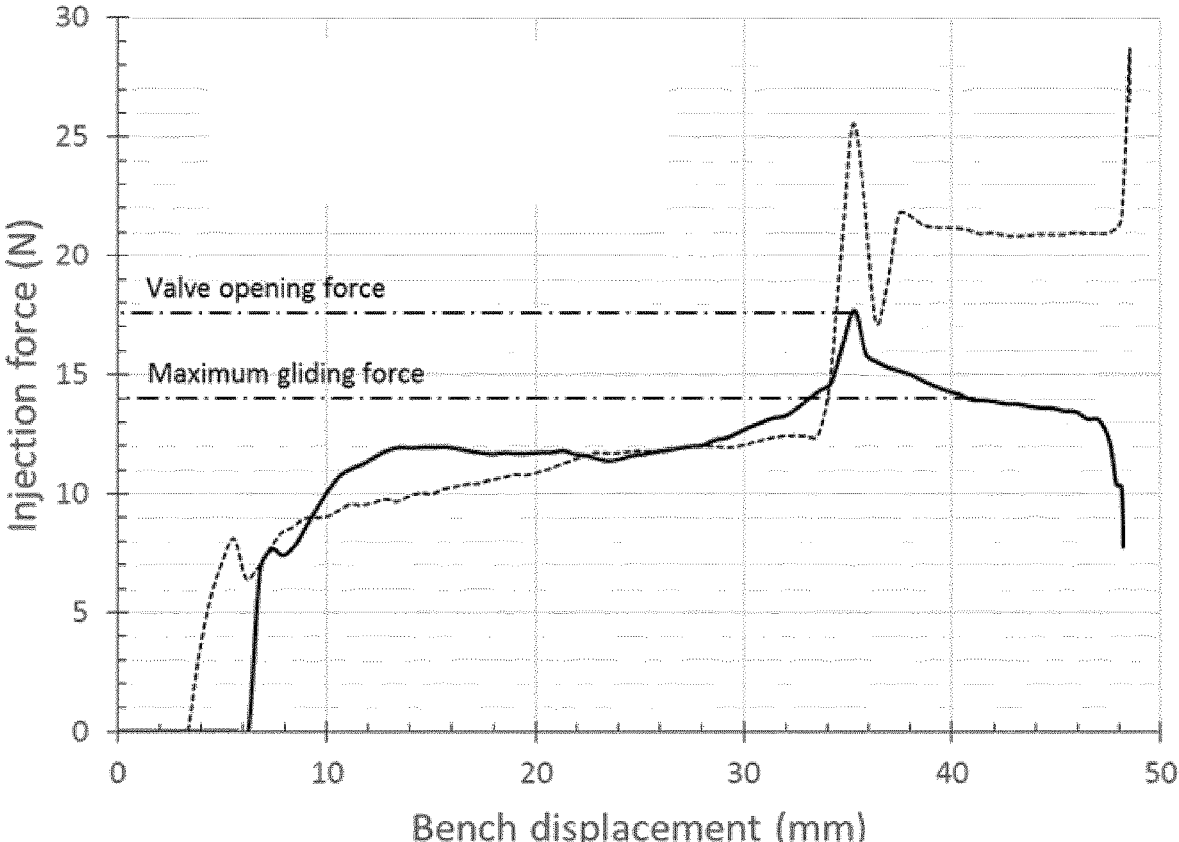
FIG. 16 is a graph that shows the evolution of the force exerted onto a valve stopper according to the disclosure, and to a stopper known from the prior art in view of the displacement of a bench.

A syringe wherein the valve stopper is in the sealing position has been used, meaning that said valve stopper does not abut the distal end of the barrel of the syringe (corresponding to FIG. 3A). Both the chambers between the distal end of the barrel and the valve stopper/stopper of the known prior art and between the valve stopper/stopper of the known prior art and the plunger stopper contain a composition to be expelled from the syringe. The syringe is mounted onto a test bench. The plunger stopper is mechanically moved in the distal direction, and the force exerted onto the plunger stopper was recorded in function of the displacement of the bench. This force corresponds to the injection force of the valve stopper/stopper of the known prior art. Said force comprises the valve opening force $F_{op}$ of the valve stopper/stopper of the known prior art, which corresponds to a local peak on the curve injection force (which corresponds to the configuration on FIG. 3B); and into gliding force when a composition is injected. Said injection force (N) of the valve stopper is represented on FIG. 16 in function of the bench displacement (mm). Both the valve opening force and the maximum gliding force are represented. The injection force of the valve stopper according to the disclosure is represented by a full line, while the injection force of the stopper of the known prior art is represented by a dotted line.

The injection force increases up to about 12 N for a bench displacement of 12 mm. This correspond to the setting in motion of the valve stopper, and requires that a certain force be applied onto said valve stopper.

The gliding force then remains substantially constant until a bench displacement of 30 mm. This corresponds to the displacement of the valve stopper in the distal direction, for injecting the first composition initially comprised between the distal end of the barrel and the valve stopper. Said force is equivalent to the force observed for the legacy design.

The injection force then suddenly increases when the bench displacement reaches 35 mm to a maximum of the curve of 17.5 N which corresponds to the valve opening force $F_{op}$.

Then, the injection force decreases to a mean value of about 14 N which corresponds to the maximum gliding force for injecting the second composition.

The valve stopper then collapses, and the second injection is ended which induces a strong decrease of the injection force.

Determination of the Average Values of the Valve Opening Force and the Gliding Force Previous test has been carried out several times for several valve stoppers of the disclosure according to the first general embodiment and several stoppers of the known prior art. The average values of the valve opening force $F_{op}$ and of the maximum gliding force for said different stoppers measured in each test are illustrated respectively in the graph of FIG. 17 and the graph of FIG. 18.

Figure 17:
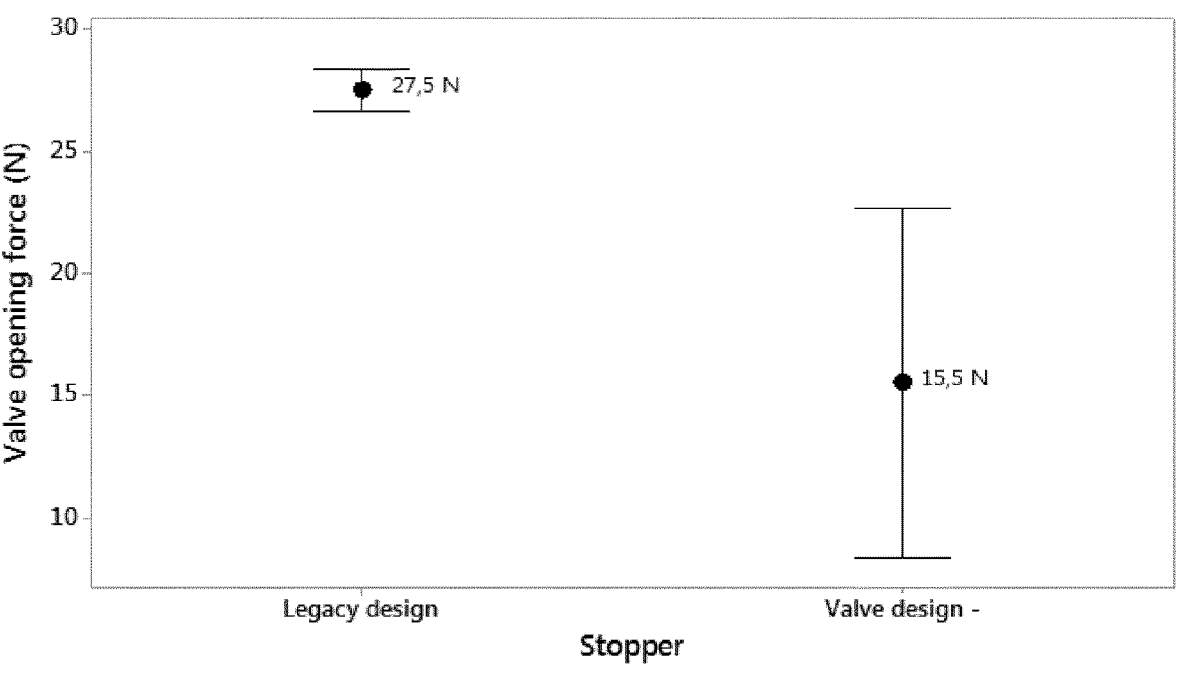
FIG. 17 is a graph that shows the force needed to open the valve, called valve opening force, for a known stopper and a valve stopper according to the disclosure.

Regarding FIG. 17, concerning the legacy design, the average value of the valve opening force is 27.5 N. The standard deviation is also represented in the graph by a vertical line delimited by two segments. The standard variation is small, which means that the different measurements lead to values of valve opening force that are close to the average value of 27.5 N.

Concerning the valve stopper of the disclosure ("valve design"), the average value of the valve opening force is 15.5 N, which is much lower than that of the legacy design. The standard deviation is high, since the tests have been carried out with valve stoppers presenting different thicknesses of membrane, which directly impacts the thickness of the split, thereby impacting also the valve opening force.

Hence, the valve stopper of the disclosure leads to much lower valve opening force than the legacy design. The valve opening force is sufficiently low to greatly facilitates the injection of the composition by the user and to prevent strain injuries, and sufficiently high to ensure tight sealing of the barrel by preventing the pharmaceutical composition from accidentally leave its chamber before its injection.

Figure 18:
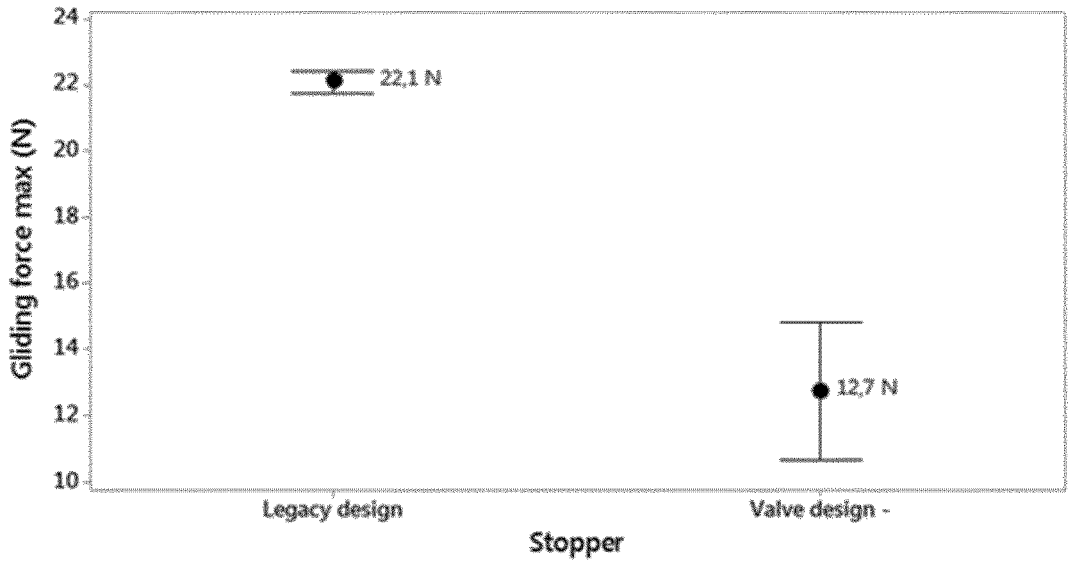
FIG. 18 is a graph that shows the maximum gliding force of a valve stopper according to the disclosure and of a stopper known from the prior art.

Regarding FIG. 18, concerning the legacy design, the average value of the maximum gliding force is 22.1 N. The standard deviation is small, which means that the different measurements lead to values of gliding force that are close to the average value of 22.1 N.

Concerning the valve stopper of the disclosure, the average value of the maximum gliding force is 12.7 N, which is much lower than that of the legacy design. The standard deviation is average, since the tests have been carried out with valve stoppers presenting different thicknesses of membrane, which impacts the weight of the valve stopper, thereby impacting also the gliding force.

Hence, the valve stopper of the disclosure leads to much lower maximum gliding force than the legacy design. This is because the one or more ribs do not form a passage for a composition, but are rather in permanent contact with the inner surface of the barrel, which prevents the valve stopper from offsetting with respect to the axis of the syringe and make the injection smoother. The valve opening force is sufficiently low to greatly facilitates the injection of the composition by the user and to prevent strain injuries, and sufficiently high to ensure tight sealing of the barrel by preventing the pharmaceutical composition from accidentally leave its chamber before its injection.

The invention claimed is:

1. A valve stopper configured to be positioned inside a barrel of an injection device for injecting at least one composition through a distal end of the barrel, the valve stopper comprising:
   a membrane comprising a proximal face having a concave shape and a distal face, the membrane being configured to separate a first, distal chamber of the barrel from a second, proximal chamber of the barrel, wherein the membrane is a monolithic membrane,
   a lateral wall extending distally, or both distally and proximally, from the membrane defining at least a distal cavity, the lateral wall comprising a circumferential sealing surface configured to sealingly engage an inner surface of the barrel,
   wherein the membrane comprises a notch extending through at least a part of a thickness of the membrane between the proximal face and the distal face, the notch being configured to transition between a closed position and an open position defining a fluid path through the membrane from the proximal face to the distal face depending on a pressure exerted by a composition onto the proximal face of the membrane, the notch maintained in the open position depending on the pressure exerted, the lateral wall extending further distally than the distal face in the closed position and the open position, and
   wherein the membrane permits transfer of fluid only from the second proximal chamber to the first distal chamber through the cavity.

2. The valve stopper of claim 1, wherein the lateral wall comprises an inner recess configured to induce collapsing of the valve stopper under a mechanical pressure exerted in a distal direction.

3. The valve stopper of claim 2, wherein the inner recess is an annular groove extending in the lateral wall of a circumference of the valve stopper.

4. The valve stopper of claim 1, wherein the sealing surface comprises three ribs, including a middle rib and two lateral ribs, and the membrane is aligned with the middle rib.

5. The valve stopper of claim 1, wherein the notch extends through a part of the membrane from the distal face of the membrane.

6. The valve stopper of claim 1, wherein the notch is a split that extends through the membrane between the proximal face and the distal face said split forming a valve configured to open or close the cavity depending on the pressure exerted by the composition onto the proximal face of the membrane.

7. The valve stopper of claim 1, wherein the notch is in the form of a line, passing through a center of the proximal face of the membrane.

8. The valve stopper of claim 7, wherein the notch further comprises two segments, each segment extending on both sides of the line.

9. The valve stopper of claim 1, wherein the distal face of the membrane has a planar or convex shape, a curvature of the distal face extending away from the proximal face.

10. The valve stopper of claim 1, wherein the notch has a length that is superior to a quarter of the diameter of the cavity and inferior to the diameter of said cavity.

11. A valve stopper configured to be positioned inside a barrel of an injection device for injecting at least one composition through a distal end of the barrel, the valve stopper comprising:
   a membrane comprising a proximal face having a concave shape and a distal face, the membrane being configured to separate a first, distal chamber of the barrel from a second, proximal chamber of the barrel,
   a lateral wall extending distally, or both distally and proximally, from the membrane defining at least a distal cavity, the lateral wall comprising a circumferential sealing surface configured to sealingly engage an inner surface of the barrel,
   wherein the membrane comprises a notch extending through at least a part of a thickness of the membrane between the proximal face and the distal face, the notch being configured to transition between a closed position and an open position defining a fluid path through the membrane from the proximal face to the distal face depending on a pressure exerted by a composition onto the proximal face of the membrane, the notch maintained in the open position depending on the pressure exerted, wherein the notch extends only in a part of the thickness of the membrane, thereby delimiting a tear part in the thickness of the membrane that is not traversed by the notch, said tear part being configured to tear along the notch under a determined pressure exerted by the composition to create the fluid path, the lateral wall extending further distally than the distal face in the closed position and the open position, and
   wherein the membrane permits transfer of fluid only from the second proximal chamber to the first distal chamber through the cavity.

12. The valve stopper of claim 11, wherein the tear part of the membrane forms a valve configured to open or close the cavity depending on the pressure exerted by the composition onto the proximal face of the membrane.

13. The valve stopper of claim 11, wherein the depth of the notch is at least 0.1 mm.

14. The valve stopper of claim 11, wherein the notch has an oblong shape, or is in the form of a cross comprising two segments that intersect at a center of the cross.

15. A medical injection device for injecting at least one composition, comprising:
   a barrel extending from a proximal end to a distal end,
   a plunger stopper adapted to be translationally movable inside the barrel,
   the valve stopper, of claim 1, arranged between the distal end of the barrel and the plunger stopper, adapted to be transitionally movable inside the barrel, wherein the lateral wall of the valve stopper sealingly engages the inner surface of the barrel.

16. The medical injection device of claim 15, said medical injection device being adapted to sequentially inject two compositions, wherein the valve stopper separates two chambers of the barrel including a first chamber between the valve stopper and the distal end of the barrel containing a first composition, and a second chamber between the valve stopper and the plunger stopper containing a second composition.

17. The medical injection device of claim 15, wherein the valve stopper has the successive following positions:
   a rest position, wherein the fluid path is closed, a sealing position, wherein the valve stopper is more distal than in the rest position, wherein the fluid path is closed, the proximal face of the membrane being subjected to a pressure that is inferior to a valve opening force of the notch, an injection position, wherein the valve stopper abuts the distal end of the barrel, the fluid path being opened due to a pressure exerted on the proximal face of the membrane that is superior to the valve opening force of the notch.

18. The medical injection device of claim 17, wherein the valve stopper further has a collapsed position wherein the plunger stopper abuts the valve stopper and said valve stopper is collapsed.

19. The medical injection device of claim 15, being a syringe.

20. The medical injection device of claim 15, wherein the proximal face of the membrane has a radius of curvature which is from 1.2 to 2.3 times greater than an inner diameter of the barrel.

* * * * *